US000001420H

United States Statutory Invention Registration [19]

[11] Reg. Number: H1420

Richardson

[43] Published: Feb. 7, 1995

[54] METHOD FOR ATTACHING DISCRETE, STRETCHED ELASTIC STRANDS TO PREDETERMINED ISOLATED PORTIONS OF DISPOSABLE ABSORBENT PRODUCTS

[76] Inventor: James W. Richardson, 6100 Center Hill Rd., Cincinnati, Ohio 45224

[21] Appl. No.: 876,338

[22] Filed: Apr. 30, 1992

[51] Int. Cl.[6] ..... A61F 13/16; A32B 31/00

[52] U.S. Cl. ..... 604/385.2; 604/358; 604/389

[58] Field of Search ..... 604/358, 373, 385.1, 604/385.2, 389, 390; 156/160–165, 176–179, 229, 259–291, 494–496, 537; 428/40, 291, 352

[56] References Cited

U.S. PATENT DOCUMENTS

| | | | |
|---|---|---|---|
| 3,860,003 | 1/1975 | Buell | 604/385.2 |
| 4,022,456 | 5/1977 | Hooper et al. | 270/65 |
| 4,081,301 | 3/1978 | Buell | 156/164 |
| 4,253,461 | 3/1981 | Strickland et al. | 128/287 |
| 4,261,782 | 4/1981 | Teed | 156/361 |
| 4,325,372 | 4/1982 | Teed | 128/287 |
| 4,333,782 | 6/1982 | Pieniak | 156/164 |
| 4,353,762 | 10/1982 | Bouda | 156/164 |
| 4,413,623 | 11/1983 | Pieniak | 604/365 |
| 4,450,026 | 5/1984 | Pieniak et al. | 156/164 |
| 4,488,923 | 12/1984 | Pieniak | 156/199 |
| 4,507,163 | 3/1985 | Menard | 156/164 |
| 4,626,305 | 12/1986 | Suzuki et al. | 156/164 |
| 4,634,482 | 1/1987 | Lammers | 156/164 |
| 4,695,278 | 9/1987 | Lawson | 604/385 |
| 4,725,468 | 2/1988 | McIntyre | 604/385.2 |
| 4,917,696 | 4/1990 | De Jonckheere | 604/385.2 |
| 5,066,289 | 11/1991 | Polski | 604/389 |
| 5,080,741 | 1/1992 | Nomura et al. | 156/201 |
| 5,091,039 | 2/1992 | Ujimoto et al. | 156/519 |
| 5,106,384 | 4/1992 | Polski | 604/390 |
| 5,151,092 | 9/1992 | Buell et al. | 604/358 |

FOREIGN PATENT DOCUMENTS 0170922 12/1986 European Pat. Off. .

*Primary Examiner*—David Brown

[57] ABSTRACT

In accordance with the present invention, a method for attaching discrete portions of stretched elastic strands to predetermined isolated portions of disposable absorbent articles having obstructing elements positioned thereon in the areas where the elastic strands are to be unattached to the disposable absorbent article, is provided. In a preferred embodiment, discrete portions of stretched, continuous elastic strands are attached to predetermined isolated portions of a continuous diaper web having obstructing elements positioned thereon in the areas where the continuous elastic strands are to be unattached to the continuous diaper web. A disposable absorbent article made in accordance to the above described method is also provided.

21 Claims, 5 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR ATTACHING DISCRETE, STRETCHED ELASTIC STRANDS TO PREDETERMINED ISOLATED PORTIONS OF DISPOSABLE ABSORBENT PRODUCTS

TECHNICAL FIELD OF THE INVENTION

The present invention relates to a method of attaching discrete, stretched elastic strands to predetermined isolated portions of disposable absorbent product comprising additional elements positioned thereon in the areas where the elastic strands are to be unjoined and relaxed, the additional elements being of a type which may interfere with the relaxing of the elastic strands. More particularly the invention relates to a method of continuously attaching elastic strands to such disposable absorbent products.

BACKGROUND OF THE INVENTION

Method and apparatus for securing one or more elastic ribbons in a stretched condition to a continuously moving web in the manufacture of garments and the like is well known in the art. This may be done either by sewing, by the use of a heat-activated coating on the elastic or by the use of a separate adhesive. It is also known that this process can be carried out in such a way that the elastic is intermittently joined to the moving web.

For aesthetic and functional reasons it is frequently preferred that the stretched elastic strands be intermittently joined to the moving web and that the individual items severed from the web be severed in the unjoined areas so that the portion of the elastic strand which is joined to the individual item will contract a discrete area of the individual item and the portion of the elastic strand which is unjoined to the individual item will contract or "snap back" and become relaxed, inactive, and non-functional. This requires that the web be free of anything that will prevent the unjoined portion of the elastic strand from contracting or "snapping back" and becoming relaxed, inactive and non-functional.

However, the design of many products will frequently require the positioning of various elements on the web in the areas where the elastic is to be unjoined to the web. If the various elements positioned on the web are of a type which will interfere with the relaxing of the unadhered areas of the elastic bands, the aesthetics and functionality of the individual items severed from the web will be greatly reduced.

An example of a product which is required to be contracted in only a discrete area, is a disposable absorbent article such as a disposable diaper. It is important that the elastic strands of the leg cuffs of the disposable diaper, contract only the area of the leg cuffs and not contract the area of the waist regions. If the elastic strands of the leg cuffs were to also contract the area of the waist region, improper fit and increased leakage would result about the waist of the wearer. Additionally, this would result in an aesthetically unappealing and less attractive end product.

The art fails to teach means for continuously joining elastic bands in discrete, spaced areas while in a stretched condition at predetermined points along a continuously moving, substantially inelastic web wherein obstructing elements are positioned in the areas where the elastic is to be unjoined to the web. Therefore, when the web is severed, the unadhered ends of the elastic strands will be restrained by the obstructing elements and will not become relaxed, inactive, and non-functional, thereby undesirably contracting the areas where the elastic is to be unjoined to the web.

Accordingly, it is an object of the present invention to provide a method for joining strands of stretched elastic in discrete areas at predetermined points on an inelastic web having obstructing elements positioned thereon.

It is a further object of the present invention to provide a method for joining continuous strands of stretched elastic in discrete, spaced areas at predetermined points along a continuously moving inelastic web having obstructing elements positioned thereon.

It is yet another object of the present invention to provide a disposable absorbent article having obstructing elements and discrete elastic strands secured thereto, the elastic strands being functional to gather discrete portions of the absorbent article without being restrained by the obstructing elements.

SUMMARY OF THE INVENTION

A method is provided for attaching discrete lengths of elastic strand to a web, the web having an obstructing element secured thereto which may interfere with the relaxing of the end portions of the elastic strands, the method comprising the steps of: providing a substrate having a first and second portion, at least part of the second portion of the substrate having at least one obstructing element positioned thereon; providing an elastomeric member in a stretched condition; intermittently applying an elastic adhesive to the elastomeric member at a first portion of the elastomeric member; applying a release agent at least to a second portion of the elastomeric member; joining the elastomeric member to the substrate whereby the first portion of the elastomeric member is disposed essentially on the first portion of the substrate and the second portion of the elastomeric member is disposed essentially on the second portion of the substrate, the second portion of the elastomeric member crossing the obstructing element; and relaxing the elastomeric member whereby the second portion of the elastomeric member relaxes and is not restrained by the obstructing element.

In a particularly preferred embodiment of the present invention, a method is provided for forming a disposable diaper having elastic leg cuffs comprising elastic strands joined to a portion of the crotch region of the disposable diaper, and having elastic side panels comprising an obstructing element in the form of a patch of elastomeric material adhesively bonded to the disposable diaper, the method comprises the steps of applying a release agent, such as mineral oil, to the end portions of a stretched elastic strand and applying elastic adhesive to a discrete middle portion of the stretched elastic strand; joining the elastic strand between the topsheet and backsheet of the diaper so that the end portions of the stretched elastic strand having the release agent applied thereto, will be positioned over the obstructing elements and the discrete middle portion of the stretched elastic strand having the elastic adhesive applied thereto, will be positioned over and will adhere to the crotch region of the disposable diaper; and severing, or otherwise relaxing, the stretched elastic strand such that the discrete middle portion of the elastic strand will contract the disposable diaper in the crotch region to form an elastic leg cuff, and the end portions of the elastic strand will "snap back" and will not contract the disposable diaper because the mineral oil will prevent the obstructing element from "grabbing", adhering to, or otherwise restraining the end portions of the elastic strand.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in connection with the accompanying drawings in which:

DETAILED DESCRIPTION OF THE INVENTION

Figure 1:
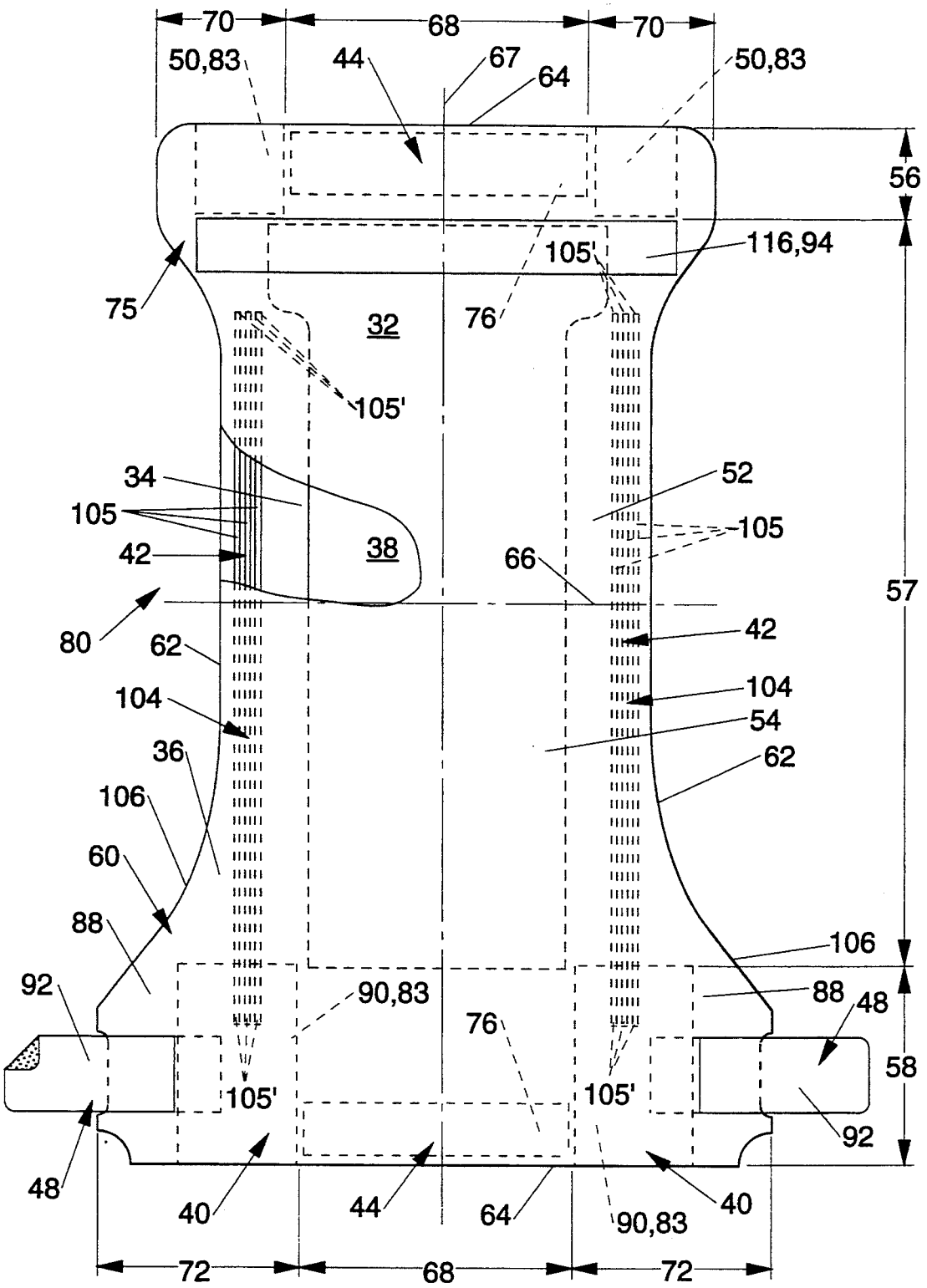
FIG. 1 is a plan view of a disposable diaper embodiment of the present invention having portions cut-away to reveal underlying structure, the outer surface of the diaper facing the viewer.

U.S. Pat. No. 4,081,301 which issued to Buell on Mar. 28, 1978, and which is hereby incorporated herein by reference, discloses an exemplary method and apparatus for continuously attaching discrete, stretched elastic strands to predetermined isolated portions of disposable absorbent products, such as disposable diapers. The Buell '301 patent teaches intermittently applying adhesive to discrete lengths of elastic ribbon at regular spaced intervals, adhering the discrete areas of the stretched elastic ribbon which are covered by adhesive to predetermined points along the length of a moisture impervious backsheet web, and severing the assembled web and the elastic in its unadhered, adhesive-free areas, whereupon the adhesive-free end portions become relaxed and inactive without affecting the functionality of the adhered portions in the ultimate assemblage.

As used herein the term "obstructing element" will refer to a feature or element which is in alignment with the elastic strands and which may restrain or interfere with the relaxing of the adhesive-free end portions of the elastic strands, thereby causing the finished product to contract or shirr undesirably. Although the obstructing elements of the preferred embodiment are described herein as elastic side panel members 90, there are many diaper embodiments having various elements which may act as obstructing elements, and it is intended that all such embodiments be covered by the present application. A non-limiting example of such an alternative embodiment of the present invention, is one wherein the elastic waistband members and/or the construction adhesive used to join the elastic waistband members to the diaper 80, act as an obstructing element. The elastic waistband members and/or the construction adhesive used to join the elastic waistband members to the diaper 80, will act as an obstructing element if the elastic waistband members and/or the construction adhesive is in alignment with the elastic strands 105 and tends to restrain or interfere with the relaxing of the adhesive-free end portions of the elastic strands 105. As used herein the term "restrain" shall refer to holding-back or preventing the adhesive-free end portions of the elastic strand 105 from becoming relaxed, inactive, and nonfunctional.

An example of an obstructing element is a patch or layer of construction adhesive positioned on the web in the area of the adhesive-free portions of the stretched elastic strands. After being severed or otherwise relaxed, the adhesive-free ends of the elastic strands may adhere to the construction adhesive and cause the disposable absorbent article to contract or shirr undesirably. Another example of an obstructing element is a high-friction element positioned on the web in the area of the adhesive-free portions of the stretched elastic strands. After being severed or otherwise relaxed, the adhesive-free ends of the elastic strands may "grab" the high-friction element and cause the disposable absorbent article to contract or shirr undesirably. An exemplary obstructing element 83, elastic side panel member 90, is shown in FIGS. 1–4. Another example of an obstructing element is the construction adhesive (not shown) which is used to secure the elastic side panel member 90 to the topsheet 34 or the backsheet 36 or both. As used herein, the term "construction adhesive" will refer to the adhesives used to join together the various elements of the diaper 80, i.e., the topsheet 34, the backsheet 36, the core 38, the elastic waistband member 76, the elastic side panel member 90, etc. As used herein the term "elastic adhesive" will refer to the adhesives used to join the elastic strands 105 to the diaper 80.

As used herein, the term "continuous web" shall refer to a web of material provided without interruption from a continuous source such as a supply roll. The term "continuous web" may also refer to an uninterrupted web of interconnected articles formed from at least one uninterrupted web of material having additional elements joined thereto. As used herein the term "continuous elastic strand" shall refer to an elastomeric member provided without interruption from a continuous source such as a supply roll or a supply box. As used herein the term "elastomeric member" shall refer to an element having some of the physical properties of natural rubber, i.e., an element capable of being stretched or expanded and of "snapping back" or substantially resuming its former shape.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 80, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, training pants, feminine hygiene garments, sanitary napkins, incontinent pads, and the like.

FIG. 1 is a plan view of the disposable diaper 80 of the present invention in its flat-out, uncontracted state (i.e., with elastic induced contraction pulled out except in the side panels wherein the elastic is left in its relaxed condition) with the portion of the diaper which faces away from the wearer, the outer surface 52, facing the viewer. As shown in FIG. 1, the diaper 80 comprises a chassis 75 comprising a containment assembly 32; elasticized side panels 40; elasticized leg cuffs 42; elasticized waistbands 44; and a fastening system 48.

The containment assembly 32 of the disposable diaper 80 preferably comprises a liquid pervious topsheet 34, a liquid impervious backsheet 36 joined with the topsheet 34, and an absorbent core 38 positioned between the topsheet 34 and the backsheet 36. While the topsheet, the absorbent core, the backsheet and the elastic members may be assembled in a variety of well known configurations, preferred disposable diaper configurations are described in U.S. Pat. No. 3,860,003 entitled "Contractible Side Portions For Disposable Diapers" which issued to K. B. Buell on Jan. 14, 1975; U.S. Pat. No. 4,695,278 entitled "Absorbent Article Having Dual Cuffs" which issued to Lawson on Sep. 22, 1987; U.S. Pat. No. 4,938,755 entitled "Absorbent Article Having A Containment Pocket" which issued to Foreman on Jul. 3, 1990; which patents are incorporated herein by reference. Preferred disposable diaper configurations are also disclosed in U.S. patent application Ser. No. 07/714,476, now abandoned, "Absorbent Article With Fastening System Providing Dynamic Elasticized Waistband Fit", Weil, et al., filed Jun. 13, 1991; U.S. patent application Ser. No. 07/715,152, now U.S. Pat. No. 5,151,092, "Absorbent Article With Dynamic Elastic Waist Feature" Having a Predisposed Resilient Flexural Hinge", Buell, et al., filed Jun. 13, 1991; and U.S. patent application Ser. No. 07/715,074, now U.S. Pat. No. 5,196,000 "Absorbent Article With Dynamic Elastic Waist Feature Comprising an Expansive Tummy Panel", Clear, et al., filed Jun. 13, 1991; which patent applications are incorporated herein by reference.

The inner surface 54 of the diaper 80 comprises that portion of the diaper 80 which is positioned adjacent to the wearer's body during use (i.e., the inner surface 54 generally is formed by at least a portion of the topsheet 34 and other components joined to the topsheet 34). The outer surface 52 comprises that portion of the diaper 80 which is positioned away from the wearer's body (i.e., the outer surface 52 generally is formed by at least a portion of the backsheet 36 and other components joined to the backsheet 36). The first waist region 56 and the second waist region 58 extend, respectively, from the end edges 64 of the periphery 60 to the crotch region 57 Of the diaper 80. The waist regions 56,58 and the crotch region 57, each comprise a central region 68. The first waist region 56 and the second waist region 58, additionally comprise a pair of side panels which typically comprise the outer lateral portions of the waist regions. The side panels positioned in the first waist region 56 are designated 70 while the side panels in the second waist region 58 are designated 72. (In the discussion that follows, unless otherwise noted, the diaper 80 will comprise a pair of side panels in each waist region. While it is not necessary that the pairs of side panels or each side panel be identical, they are preferably mirror images one of the other.) In a preferred embodiment of the present invention, the side panels 72 positioned in the second waist region 58 are elastically extensible in the lateral direction (i.e., elasticized side panels 40). (The lateral direction (x direction or width) is defined as the direction parallel to the lateral centerline 66 of the diaper 80; the longitudinal direction (y direction or length) being defined as the direction parallel to the longitudinal centerline 67; and the axial direction (Z direction or thickness) being defined as the direction extending through the thickness of the diaper 80.)

FIG. 1 shows a preferred embodiment of the diaper 80 in which the topsheet 34 and the backsheet 36 have length and width dimensions generally larger than those of the absorbent core 38. The topsheet 34 and the backsheet 36 extend beyond the edges of the absorbent core 38 to thereby form the periphery 60 of the diaper 80. The periphery 60 defines the outer perimeter or, in other words, the edges of the diaper 80. The periphery 60 comprises the longitudinal edges 62 and the end edges 64.

The containment assembly 32 of the diaper 80 is shown in FIG. 1 as comprising the chassis 75 of the diaper 80. The containment assembly 32 comprises at least an absorbent core 38 and preferably an outer covering layer comprising the topsheet 34 and the backsheet 36. For unitary absorbent articles, the containment assembly 32 comprises the main structure of the diaper with other features added to form the composite diaper structure. Thus, the containment assembly 32 for the diaper 80 generally comprises the topsheet 34, the backsheet 36, and the absorbent core 38.

The absorbent core 38 may be any absorbent means which is generally compressible, conformable, nonirritating to the wearer's skin, and capable of absorbing and retaining liquids such as urine and other certain body exudates.

The absorbent core 38 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 38 should, however, be compatible with the design loading and the intended use of the diaper 80. Further, the size and absorbent capacity of the absorbent core 38 may be varied to accommodate wearers ranging from infants through adults.

A preferred embodiment of the diaper 80 has an asymmetric, modified T-shaped, absorbent core 38 having ears in the first waist region 56 but a generally rectangular shape in the second waist region 58. This configuration allows wider elasticized side panels 40 in the second waist region 58. An exemplary absorbent structure for use as the absorbent core 38 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; and U.S. Pat. No. 4,888,231 entitled "Absorbent Core Having A Dusting Layer" issued to Angstadt on Dec. 19, 1989; also describe absorbent structures that are useful in the present invention. The absorbent core 38 is preferably the commercially successful absorbent member described in U.S. Pat. No. 4,834,735, entitled "High Density Absorbent Members Having Lower Density and Lower Basis Weight Acquisition Zones", issued to Alemany and Berg on May 30, 1989. Each of these references are incorporated herein by reference.

In a preferred alternate embodiment of the present invention, the absorbent core comprises two distinct webs or layers comprising an acquisition/distribution core and a storage core. The acquisition/distribution core is positioned between the topsheet 34 and the storage core, and the storage core is positioned between the acquisition/distribution core and the backsheet 36. The acquisition/distribution core has a top surface area which preferably is at least about 15% of the top surface areas of the storage core, but which is smaller than the top surface area of the storage core. The acquisition/-distribution core is positioned relative to the storage core so that none of its surface area extends beyond the boundaries of the storage core. As detailed below, the acquisition/distribution core preferably comprises a web of chemically stiffened cellulosic fibers, although binding means such as non-stiffened cellulosic fibers, synthetic fibers, chemical additives, and thermoplastic fibers can be added to increase the physical integrity of the web. The storage core preferably comprises an airlaid web of superabsorbent material and fiber material, preferably airfelt. Optionally, and most preferably, a pervious sheet (e.g., a tissue sheet) or other scrim may be positioned between the acquisition/distribution core and the storage core to increase the integrity of the absorbent core 38 during processing and/or use.

The acquisition/distribution core serves to quickly collect discharged body fluids, to quickly transport the fluid from the point of initial contact to other parts of the acquisition/distribution core, and to temporarily hold such discharged body fluids until they can be absorbed by the storage core. The distribution function of the acquisition/distribution core is of particular importance in order to more fully utilize the capacity of the storage core. Thus, while the acquisition/distribution core may comprise a wide variety of absorbent materials, it preferably comprises fiber material that can rapidly transport fluid and not collapse upon being wetted so that the acquisition/distribution core can effectively acquire and distribute second and successive voids of fluid as well as minimal amount (<2%) of superabsorbent material (due to the slowness of their uptake and gel blocking). An absorbent core comprising two distinct webs or layers comprising an acquisition/distribution core and a storage core is more fully described in U.S. patent application Ser. No. 843,706, now U.S. Pat. No. 5,234,423, "Absorbent Article with Elastic Waist Feature and Enhanced Absorbency", Alemany, et al., P&G Case 4576, filed Feb. 28, 1992 and incorporated herein by reference.

The backsheet 36 is positioned adjacent the absorbent core 38 and is preferably joined thereto by attachment means (not shown) such as those well known in the art. For example, the backsheet 36 may be secured to the absorbent core 38 by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 36 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 36 prevents the exudates absorbed and contained in the absorbent core 38 from wetting articles which contact the diaper 80 such as bedsheets and undergarments. The backsheet 36 may thus comprise a woven or nonwoven material, polymeric films such as thermoplastic films of polyethylene or polypropylene, or composite materials such as a film-coated nonwoven material. Preferably, the backsheet is a film having a thickness of from about 0.012 mm (0.5 mil) to about 0.051 mm (2.0 mils). More preferably the backsheet is a film embossed to a caliper of about 0.051 mm (2.0 mils) to about 0.254 mm (10.0 mils). In a preferred embodiment the backsheet is a film embossed to a caliper of about 0.127 mm (5.0 mils).

Preferred polymeric films for use as the backsheet contain a high content of linear low density polyethylene. Particularly preferred materials for the backsheet include blends comprised of about 45–97% linear low density polyethylene and about 3–55% polypropylene. Exemplary films for use as the backsheet of the present invention are manufactured by Tredegar Industries, Inc. of Terre Haute, Ind. under the designation X-8834 blend for blown films and X-5475 blend for cast films. The backsheet 36 is preferably embossed (typically, to a caliper of about 0.127 mm (5.5 mils)) and/or matte finished to provide a more clothlike appearance. Further, the backsheet 36 may permit vapors to escape from the absorbent core 38 (i.e., breathable) while still preventing exudates from passing through the backsheet 36.

The size of the backsheet 36 is dictated by the size of the absorbent core 38 and the exact diaper design selected. In a preferred embodiment, the backsheet 36 has a modified hourglass shape extending beyond the absorbent core 38 a minimum distance of at least about 1.3 cm to about 2.5 cm (about 0.5 to about 1.0 inch) around the entire diaper periphery 60. Preferably, the backsheet 36 is much wider than the absorbent core 38 in the second waist region 58 so that the side panels 72 in the second waist region 58 are generally wider in the lateral direction than the side panels 70 in the first waist region 56.

The topsheet 34 is positioned adjacent the absorbent core 38 and is preferably joined thereto and to the backsheet 36 by attachment means (not shown) such as those well known in the art. Suitable attachment means are described with respect to joining the backsheet 36 to the absorbent core 38. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. As used herein, the term "joined" also encompasses configurations whereby two discrete elements are affixed to each other, and configurations whereby two elements are unitary (i.e., each element may comprise discrete components affixed thereto, but the two elements comprise at least one common component). In a preferred embodiment of the present invention, the topsheet 34 and the backsheet 36 are joined directly to each other in the diaper periphery 60 and are indirectly joined together by directly joining them to the absorbent core 38 by the attachment means (not shown).

The topsheet 34 is compliant, soft feeling, and non-irritating to the wearer's skin. Further, the topsheet 34 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 34 is made of a hydrophobic material to isolate the wearer's skin from liquids contained in the absorbent core 38.

There are a number of manufacturing techniques which may be used to manufacture the topsheet 34. For example, the topsheet 34 may be a nonwoven web of fibers. When the topsheet comprises a nonwoven web, the web may be spunbonded, carded, wet-laid, melt-blown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 inches). Preferably, the topsheet has a basis weight from about 18 to about 25 grams per square meter. A suitable topsheet is manufactured by Veratec, Inc., a Division of International Paper Company, of Walpole, Mass. under the designation P-8.

The diaper 80 further comprises an elasticized waistband 44 disposed adjacent the end edge 64 of the diaper 80 in the first waist region 56. The waistband of the diaper 80 is that portion which is intended to be placed adjacent the wearer's waist. The elasticized waistband 44 provides a member that maintains a defined area coverage, contacts the wearer's waist, and is elastically extensible in at least the lateral direction so as to dynamically fit against the waist of the wearer and to dynamically conform to the waist of the wearer so as to provide improved fit.

Figure 2:
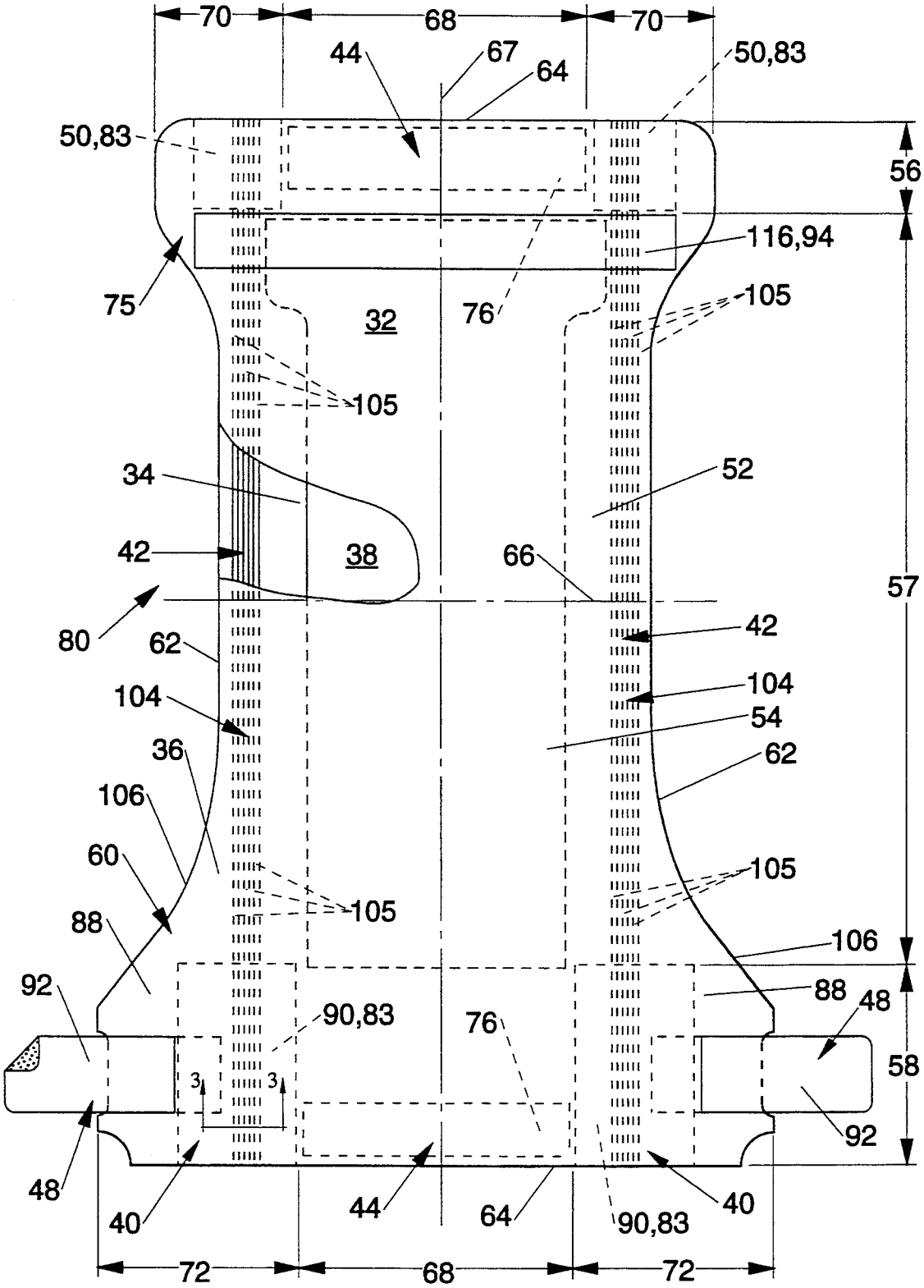
FIG. 2 is a plan view of the disposable diaper shown in FIG. 1, showing the elastic strands 105 in a stretched condition, i.e., prior to severing or otherwise relaxing the elastic strands 105.

While the elasticized waistband 44 can comprise a separate element affixed to the containment assembly 32 of the diaper 80, the waistband is preferably an extension of other elements of the diaper 80 such as the topsheet 34 or the backsheet 36 or both and an elastomeric material joined thereto. Disposable diapers are often constructed so as to have two elasticized waistbands; one positioned in the first waist region 56 and one positioned in the second waist region 58. As discussed herein, the diaper 80 at least has an elasticized waistband 44 disposed in at least the central region 68 of the first waist region 56. Preferably, as shown in FIGS. 1 and 2, another elasticized waistband is disposed in the second waist region 58, preferably between the elasticized side panels 40.

In a preferred embodiment of the present invention shown in FIG. 1, the elasticized waistband 44 comprises an elastic waistband member 76 interposed between the topsheet 34 and the backsheet 36 and operatively associated with either or both the topsheet 34 and the backsheet 36 to gather the first waist region 56 of the diaper 80. An example of such an elasticized waistband for use herein is the elasticized waistband disclosed in U.S. Pat. No. 4,515,595 entitled "Disposable Diapers With Elastically Contractible Waistbands", which issued to Kievit and Osterhage on May 7, 1985, and which patent is incorporated herein by reference. Any suitable elastomeric material as known in the art may be used as the elastic waistband member 76 of the present invention. Examples of suitable elastomeric materials include elastomeric films, elastomeric foams such as polyurethane foams or crosslinked natural rubber foams; formed elastic scrim; elastomeric films such as heat shrinkable elastic materials; elastomeric film laminates such as a laminate of a heat-shrinkable elastomeric film and a resilient member; elastomeric stretch laminates such as "zero strain" stretch laminates or mechanically stretched pretensioned stretch laminates; and elastic strands made from rubber, LYCRA, or other materials. In a preferred embodiment, the elastic waistband member 76 comprises a KRATON based elastomer film, which films are available from the Exxon Chemical Company, 5200 Bay Way Drive, Baytown, Tex. 77520. Other embodiments of preferred constructions for the elasticized waistband are the elastic waist features described in commonly assigned, co-pending, U.S. patent application Ser. No. 07/750,775, filed Aug. 22, 1991 in the name of K. B. Buell et al., "Absorbent Article With Dynamic Elastic Waist Feature Having A Predisposed Resilient Flexural Hinge"; the specification and drawings of which are incorporated herein by reference, now U.S. Pat. No. 5,151,092.

In an alternative embodiment, the elasticized waistband in the second waist region 58 (or in the first waist region 56 if elasticized side panels are disposed therein) and the elasticized side panels 40 can be formed by securing a single piece of elastomeric material to the diaper 80 in both the side panels 72 and the central region 68 of the second waist region 58. Thus, the elasticized waistband 44 and the elasticized side panels 40 can be formed from the same piece of material to form a unitary structure. An example of such an elasticized waistband/side panel configuration is disclosed in the hereinbefore referenced U.S. Pat. No. 4,887,067 issued to Wood, et al. on Aug. 15, 1989, and which patent is incorporated herein by reference.

The diaper 80 is further provided with a fastening system 48 for forming a waist closure. The fastening system 48 maintains the first waist region 56 and the second waist region 58 in an overlapping configuration to maintain the diaper on the wearer.

The diaper 80 may comprise any type of fastening system 48 that is well known in the art. As shown in FIG. 1, the fastening system 48 comprises a first fastening component, tape tab 92, attached to the side edges 62 of the diaper 80 in the second waist region 58. The fastening system 48 preferably also comprises a complementary second fastening component, landing member 94, engageable with the first fastening component. An exemplary fastening system 48 wherein the first and second fastening components each comprise mechanical closure elements comprising hook and loop fastening materials is disclosed in U.S. Pat. No. 4,869,724 entitled "Mechanical Fastening Systems With Adhesive Tape Disposal Means For Disposable Absorbent Articles" issued to Scripps on Sep. 26, 1989. Fastening systems utilizing mechanical closure elements are also disclosed in U.S. Pat. No. 4,846,815 entitled "Disposable Diaper Having An Improved Fastening Device" issued to Scripps on Jul. 11, 1989; and U.S. Pat. No. 4,894,060 entitled "Disposable Diaper With Improved Hook Fastener Portion" issued to Nestegard on Jan. 16, 1990. A fastening system having combination adhesive/mechanical closure elements is described in U.S. Pat. No. 4,946,527 entitled "Pressure-Sensitive Adhesive Fastener And Method of Making Same" issued to Battrell on Aug. 7, 1990. Each of these patents are incorporated herein by reference. A preferred fastening system is a two point fastening system described in U.S. patent application Ser. No. 07/714,476, now abandoned entitled "Absorbent Article with Fastening System Providing Dynamic Elasticized Waistband Fit", filed Jun. 13, 1991 in the name of Weil et al., which patent application is incorporated herein by reference. Although a two point fastening system is preferred, the hook fastening material of the two point fastening system has been removed from FIGS. 1 and 2 for clarity. The fastening system 48 shown in FIG. 1, comprises an adhesive tape tab fastening system comprising a tape tab 92 having an adhesive attachment layer and a landing member 94 comprising a reinforcing strip 116 joined to the backsheet 36. Examples of such adhesive tape tab fastening systems are disclosed in U.S. Pat. No. 3,848,594 entitled "Tape Fastening System for Disposable Diaper" issued to Buell on Nov. 19, 1974; and the adhesive tape tabs, reinforcing strip, and indicia means disclosed in U.S. Pat. No. B1 4,662,875 entitled "Absorbent Article" issued to Hirotsu and Robertson on May 5, 1987. Each of these patents are incorporated herein by reference. The reinforcing strip 116 of the landing member 94 may comprise any of a number of configurations and materials secured to the backsheet 36 of the diaper 80. The reinforcing strip 116 is preferably a separate member secured to the backsheet 36 to form a portion of the outer surface 52 of the diaper 80. A preferred reinforcing strip 116 comprises a sheet of biaxially oriented polypropylene film.

In a preferred embodiment, the diaper 80 also comprises a positioning patch 50. As shown in FIG. 1, the positioning patches 50 each comprise a rectangular-shaped piece of material which extends from the end edge 64 of the diaper 80 inward towards the center of the diaper. The positioning patches 50 are preferably positioned between the topsheet 34 and the backsheet 36. The positioning patches 50 preferably comprise a patch of elastomeric foam. More preferably, during manufacture of the diaper, the positioning patches 50 are formed of the same material as the elastic side panel member 90 with the elastic side panel member 90 of one diaper and the positioning patch 50 of the adjacent diaper being formed from the same segment of material that is then cut after the diaper is completed. When using the preferred two point fastening system of the aforementioned U.S. patent application Ser. No. 07/714,476, now abandoned positioning patch 50 will preferably be located subjacent an array of thermoplastic prongs, or hooks, which form a component of a hook and loop type fastening material. The positioning patch 50 raises the array of thermoplastic prongs in the Z direction (thickness) to allow the prongs to come in better contact with a complimentary loop fastener material. Alternatively, the positioning patch 50 may be used to form an elasticized side panel 40 in the first waist region 56 using the method described herein with regard to the elasticized side panels 40 of the second waist region 58.

The positioning patch 50 of the present invention and/or the construction adhesive (not shown) used to join the positioning patch 50 to the disposable diaper 80, are also referred to as obstructing elements 83, because they are in alignment with the elastic strands 105 of the elastic gasketing cuff 104 and will tend to restrain or interfere with the relaxing of the adhesive free end portions of the elastic strands 105 in the first waist region 56.

In a preferred embodiment, the diaper also comprises elasticized side panels 40 disposed in the second waist region 58. (As used herein, the term "disposed" is used to mean that an element(s) of the diaper is formed (joined and positioned) in a particular place or position as an unitary structure with other elements of the diaper or as a separate element joined to another element of the diaper.) The elasticized side panels 40 provide an elastically extensible feature that provides a more comfortable and contouring fit by initially conformably fitting the diaper to the wearer and sustaining this fit throughout the time of wear well past when the diaper has been loaded with exudates since the elasticized side panels allow the sides of the diaper to expand and contract. Further, the elasticized side panels 40 develop and maintain wearing forces (tensions) that enhance the tensions developed and maintained by the fastening system 48 to maintain the diaper 80 on the wearer and enhance the waist fit. The elasticized side panels 40 further provide more effective application of the diaper 80 since even if the diaperer pulls one elasticized side panel 40 farther than the other during application (asymmetrically), the diaper 80 will "self-adjust" during wear. While the diaper 80 of the present invention preferably has the elasticized side panels 40 disposed in the second waist region 58; alternatively, the diaper 80 may be provided with elasticized side panels 40 disposed in the first waist region 56 or in both the first waist region 56 and the second waist region 58.

As shown in FIG. 1, each elasticized side panel 40 comprises an ear flap 88 and an elastic side panel member 90 operatively associated therewith. Each ear flap 88 comprises that portion of the side panel 72 that extends laterally outwardly from and along the side edge of the absorbent core 38 to the longitudinal edge 62 of the diaper 80. The ear flap 88 generally extends longitudinally from the end edge 64 of the diaper 80 to the portion of the longitudinal edge 62 of the diaper 80 that forms the leg opening (this segment of the longitudinal edge 62 being designated as leg edge 106). In a preferred embodiment of the present invention, each ear flap 88 in the second waist region 58 is formed by the portions of the topsheet 34 and the backsheet 36 that extend beyond the side edge of the absorbent core 38.

In a preferred embodiment of the present invention, the elastic side panel members 90 are operatively associated with the diaper 80 in the ear flaps 88, preferably between the topsheet 34 and the backsheet 36, so that the elastic side panel members 90 allow the elasticized side panels 40 to be elastically extensible in the lateral direction (laterally elastically extensible). As used herein, the term "elastically extensible" means a segment or portion of the diaper that will elongate in at least one direction (preferably the lateral direction for the side panels and the waistbands) when tensional forces (typically lateral tensional forces for the side panels and the waistbands) are applied, and will return to about its previous size and configuration when the tensional forces are removed. Generally, elastomeric materials useful in the present invention will contractively return to at least about 75% of their original configuration within about 5 seconds or less upon stretch and immediate release thereof (i.e., a "snappy" elastic).

The elastic side panel member 90 may be operatively associated with the ear flap 88 by any means well known in the art. Commonly assigned, co-pending, U.S. patent application Ser. No. 07/821,654, now abandoned, filed Jan. 16, 1992 in the name of D. J. K. Goulait and J. E. Carstens, "Method of Manufacturing and Absorbent Article Having Elastically Extensible Portions", describes a disposable diaper having an elastic side panel member operatively associated with each ear flap. Commonly assigned, co-pending, U.S. patent application Ser. No. 07/750,775, now U.S. Pat. No. 5,151,092, filed Aug. 22, 1991 in the name of K. B. Buell, et al., "Absorbent Article With Dynamic Elastic Waist Feature Having a Predisposed Resilient Flexural Hinge", describes a particularly preferred means of operatively associating the elastic side panel member with the ear flaps of a disposable diaper, which comprises joining the elastic side panel member between the topsheet and backsheet in the ear flap to form a laminate, and mechanically stretching the laminate such that the ear flap is permanently elongated and the laminate is elastically extensible in the direction of initial stretching, once the initial stretching forces are removed from the laminate. Each of these patent applications are incorporated herein by reference.

The elastic side panel members 90 may take on a number of different sizes, shapes, configurations and materials. For example, the elasticized side panels 40 may be formed from one or a plurality of elastic side panel members 90 operatively associated in each ear flap 88; the elastic side panel members may have varying widths and lengths; or the elastic side panel members may comprise relatively narrow strands of elastomeric material or a larger area elastomeric patch. Suitable elastomeric materials for use as the elastic side panel members 90, include elastomeric scrims, natural rubber films, urethane or other elastomeric foams. A particularly preferred elastomeric material is a natural rubber foam available from NRF Inc., P.O. Box 4549, Middletown, R.I. 02840, and marketed as Crosslinked Natural Rubber Foam #0212 or Crosslinked Natural Rubber Foam #0214.

As shown in FIGS. 1 and 2, the elastic side panel member 90 comprises a patch of elastomeric material (elastomeric patch) that is preferably positioned in the ear flap 88 in the second waist region 58. Although the elastic side panel member 90 may longitudinally extend through the entire length of the ear flap 88, it is preferred that the elastic side panel member 90 longitudinally extend through only a portion of the length of the ear flap 88.

The elastic side panel members 90 of the present invention and/or the construction adhesive (not shown) used to join the elastic side panel members 90 to the disposable diaper 80, are also referred to as obstructing elements 83, because they are in alignment with the elastic strands 105 of the elastic gasketing cuff 104 and will tend to restrain or interfere with the relaxing of the adhesive free end portions of the elastic strands 105 in the second waist region 58.

The diaper 80 preferably further comprises elasticized leg cuffs 42 for providing improved containment of liquids and other body exudates. Each elasticized leg cuff 42 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled "Contractable Side Portions For a Disposable Diaper" issued to Buell on January 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. Each of these patents are incorporated herein by reference. While a disposable absorbent article may comprise elasticized leg cuffs 42 configured so as to be similar to any of the leg bands, side flaps, barrier cuffs, or elastic cuffs described above, the preferred disposable absorbent article, diaper 80 shown in FIG. 1, will comprise at least an elastic gasketing cuff 104 with one or more elastic strands 105. In a preferred embodiment the elasticized leg cuff 42 additionally comprises an inner barrier cuff (not shown) as described in the above-referenced U.S. Pat. No. 4,695,278.

The elastic gasketing cuffs 104 may comprise one or several elastic strands. In a particularly preferred embodiment of the present invention, shown in FIG. 1, the elastic gasketing cuffs 104 will comprise three elastic strands 105 which are positioned between the topsheet 34 and the backsheet 36, are operatively associated with the diaper 80 in the crotch region 57, and which have relaxed, inactive, nonfunctional adhesive-free end portions 105'.

The diaper 80 has elastic side panel members 90, positioning patches 50 and elastic waistband members 76, which are adhesively joined in the first waist region 56 and second waist region 58. These may act as obstructing elements which may restrain or interfere with the relaxing of the adhesive-free end portions of the elastic strands, thereby causing the finished diaper to contract or shirr undesirably. Therefore, a specific process must be followed when intermittently applying an elastic strand to a diaper or diaper web, having obstructing elements positioned thereon.

Figure 3:
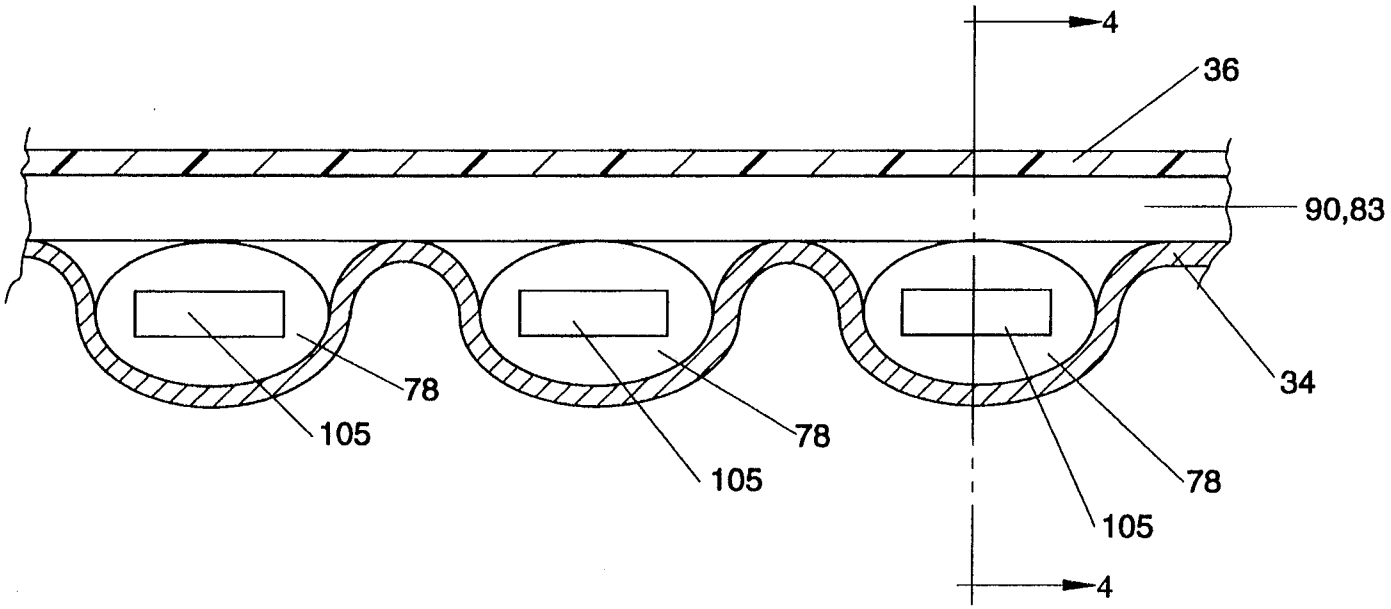
FIG. 3 is a fragmentary sectional view of the disposable diaper shown in FIG. 2 taken along section line 3—3 of FIG. 2.
Figure 4:
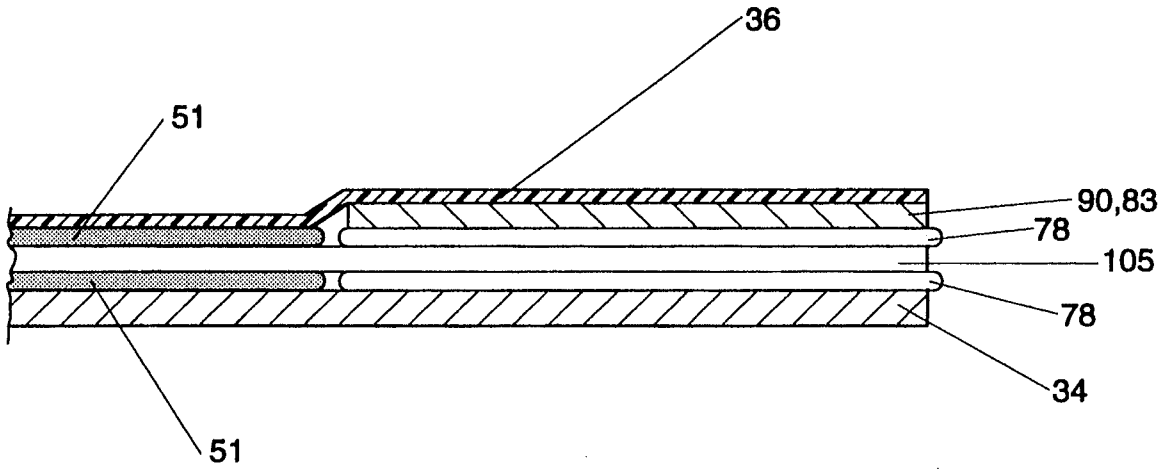
FIG. 4 is a fragmentary sectional view of the disposable diaper of FIG. 3 taken along section line 4—4 of FIG. 3.

The preferred embodiment of the process of the present invention, a process for forming the elastic gasketing cuffs 104, consists of the following steps: stretching the elastic strands 105; applying a release agent to at least the end portions of the elastic strands 105 (i.e., the portions of the elastic strands which will superpose the obstructing elements 83 in the first waist region and the second waist region 56, 58); applying an elastic adhesive to the portion of the elastic strands 105 which will be operatively associated with the diaper 80; joining the elastic strands to the disposable absorbent article, preferably between the topsheet 34 and backsheet 36 as shown in FIGS. 2, 3 and 4; and relaxing the elastic strands such that the portion having the elastic adhesive applied thereto will contract a portion of the crotch region 57 and form an elastic gasketing cuff 104, and the adhesive-free end portions 105' will become relaxed, inactive and nonfunctional. The end portions will become relaxed, inactive, and nonfunctional without being restrained by the obstructing elements 83, because the end portions have been treated with a release agent.

The step of stretching the elastic strands may be accomplished manually or by any means well known in the art. In a preferred embodiment of the present invention, the elastic strands 105 will be continuous elastic strands which are applied to a continuous diaper web from which the individual diapers will be severed. One method of stretching continuous elastic strands is to feed the continuous elastic strands into a low pressure nip formed between a pair of metering rolls and thereafter feed the continuous elastic strand into the nip formed between a pair of combining rolls which combine the various webs that make up the continuous diaper web. The metering rolls act to meter the continuous elastic strands being fed to the combining rolls at an extremely accurate and predetermined rate. This method of metering a continuous elastic strand is described in greater detail in the aforementioned U.S. Pat. No. 4,081,301 to Buell, which is incorporated herein by reference.

One material which has been found to be suitable as the elastic strand 105, is an elastomeric member having a cross-section of 0.18 mm. by 1.5 mm. and made from natural rubber as available from East Hampton Rubber Thread Company of Stuart Va., under the trademark L-1900 Rubber Compound. Other suitable materials for the elastic strand 105 are natural rubber, such as elastic tape sold under the trademark Fulflex 9211 by Fulflex Company of Scotland, N.C. The elastic strand 105 may also comprise a wide variety of materials as are well known in the art including elastomeric films, polyurethane films, and formed elastic scrim. In addition, the elastic strand 105 may take a multitude of configurations. For example, the width of the elastic strand 105 may be varied from about 0.25 mm (0.01 inches) to about 25 mm. (1.0 inch) or more; the elastic strand 105 may comprise a single strand of elastic material or may comprise several parallel or nonparallel strands of elastic material.

The step of applying release agent to the elastic strands 105 may be accomplished manually or by any other means well known in the art. The method of applying the release agent to the elastic strands 105 may vary according to the type of release agent used, e.g., a release agent in a liquid form may be applied differently than a release agent in a solid or powder form. In the preferred embodiment of the present invention, the release agent is a liquid which is applied to continuous elastic strands 105 by an applicator such as that shown in FIG. 5.

Figure 5:
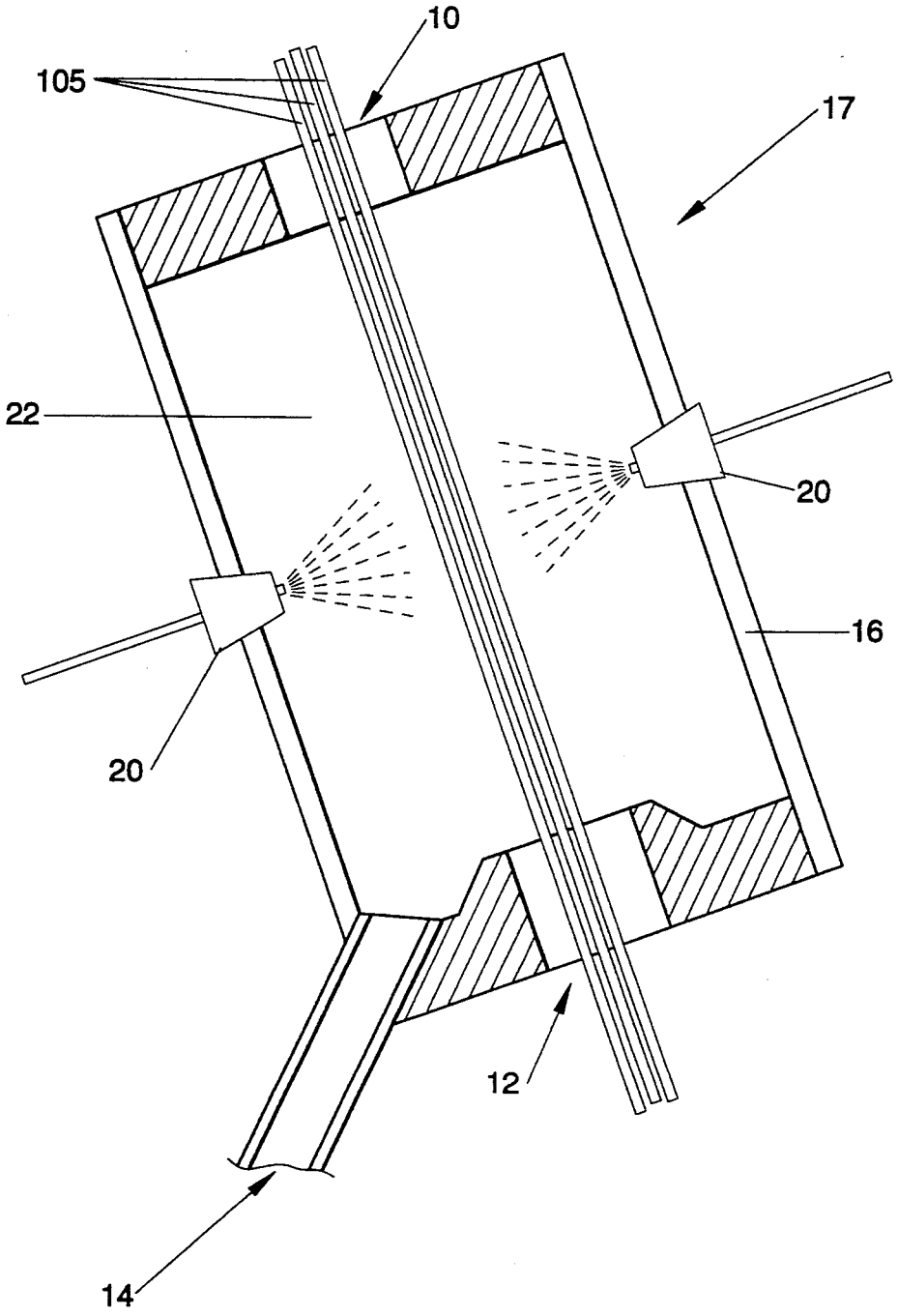
FIG. 5 is a simplified sectional side elevation view of a preferred release agent applicator.

Referring to FIG. 5 the release agent applicator 17 comprises a generally cylindrical chamber 16 having an inlet passage 10 and an outlet passage 12, two spray heads 20, and a recirculation passage 14. The continuous strands of elastic are passed through the inlet passage 10 and the outlet passage 12 of the applicator 17 such that the elastics 105 do not touch the side of the inlet passage 10 or the outlet passage 12, and do not touch the chamber 16. The spray heads 20 spray finely atomized droplets of release agent onto the continuous elastic strands 105. Preferably the spraying of finely atomized release agent occurs intermittently, and is carefully timed to correspond with portions of the continuous elastic strands 105 which will be positioned over the obstructing elements 83 of the diaper 80. The recirculation passage 14 draws, under vacuum, any excess release agent from the inner chamber 22. This insures that the continuous elastic strands 105 will only receive release agent in accordance with the accurately timed intermittent spray. Additionally, the recirculation passage 14 allows the excess release agent to be recirculated to the spray heads 20 and reused. It should be understood, that although the spray heads 20 are preferably operated intermittently to apply release agent at predetermined spaced intervals along the length of the continuous elastic strands 105, the spray heads 20 may spray continuously to coat the entire length of the continuous elastic strand 105 with a release agent. This is because some elastic adhesives may work well and be substantially unaffected by some release agents.

The release agent 78 shown in FIGS. 3 and 4, may be any substance which can be applied to the elastic strands 105 and will prevent the elastic strands 105 from adhering, bonding, or sticking to the obstructing elements 83. Preferably the release agent 78 will be inexpensive and easy to apply at high operating speeds. There is a wide range of materials which would act as suitable release agents, and the release agent may come in various forms, e.g., solid, liquid, powder, etc. The most suitable release agent for a particular application may vary according to the particular type of obstructing element or elements present. Examples of suitable release agents for use with the diaper 80 described herein, would include hot melt waxes, wax emulsions, petroleum distillates, synthetic petroleum distillates, silicones, and mineral oils. A preferred release agent for use with the diaper 80 described herein, is mineral oil. A particularly preferred mineral oil is KAYDOL (350 sus viscosity) commercially available from Witco Corp., Sonneborn Division, Melrose Park, Ill. 60160. Other suitable mineral oils include White NF Mineral Oil (75 sus viscosity) available from Amoco Oil Company, 200 E. Randolph, Chicago, Ill. 60601; CRYSTOSOL (75 sus viscosity) available from IGI Petroleum Specialties, Inc., 221 W. Grand Ave., Montvale, N.J. 07645; BRITOL (300 sus viscosity) and ERVOL (125 sus viscosity), both of which are available from the aforementioned Witco Corporation.

The step of applying elastic adhesive to the elastic strands 105 may be accomplished manually or by any other means well known in the art. The method of applying elastic adhesive to the elastic strands 105 may vary according to the type of elastic adhesive used. The adhesive may be applied as a uniform continuous layer of adhesive, a pattern layer of adhesive, or an array of separate lines, spirals, or spots of adhesive. The adhesive will preferably be applied as an open pattern network of filaments of adhesives as is disclosed in U.S. Pat. No. 4,573,986 entitled "Disposable Waist Containment Garment", which issued to Minetola and Tucker on Mar. 4, 1986, and which is incorporated herein by reference. An exemplary attachment means comprises several lines of adhesive filaments swirled into a spiral pattern such as is illustrated by the apparatus and methods shown in U.S. Pat. No. 3,911,173 issued to Sprague Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patent are incorporated herein by reference.

The elastic adhesive 51 shown in FIG. 4, should be flexible and of sufficient adhesiveness to hold the elastic strands 105 to the diaper. The elastic adhesive may be any substance which can be applied to the elastic strands 105 and will adhere the elastic strands 105 to the diaper 80 without inhibiting the elastic qualities of the elastic strands, i.e., will allow the elastic strands to become operatively associated with the diaper. Preferably, the elastic adhesive 51 will be inexpensive and easy to apply at high operating speeds. There is a wide range of materials which would act as suitable elastic adhesives. The most suitable elastic adhesive may vary according to the particular type of elastomeric members and diaper materials being used. A preferred elastic adhesive for use with the diaper 80 described herein, is a hot melt adhesive marketed by Findley Adhesives Incorporated, Elm Grove, Wis. as Findley Adhesive No. H2247-01.

The step of joining the stretched elastic strands to the disposable absorbent article, may be accomplished manually or by any other means well known in the art. In a preferred embodiment shown in FIGS. 2, 3, and 4, the elastic strands 105 will be positioned between the topsheet 34 and backsheet 36. Referring to FIG. 2, the stretched elastic strands 105 will extend from about the end edge 64 of the first waist region 56 to about the end edge 64 of the second waist region 58, will be positioned between the topsheet 34 and backsheet 36, and will be positioned adjacent to each longitudinal side edge 62 in the crotch region 57 such that in a normally relaxed configuration, the elastic strands 105 effectively contract or gather the crotch material to provide an elastic retraction line colinear with the material of the elastic strand 105 to form an elastic gasketing cuff 42 on each side of the diaper 80. FIG. 3 is a fragmentary sectional view of the disposable diaper shown in FIG. 2 taken along section line 3-3 of FIG. 2. FIG. 3 shows the stretched elastic strands 105 positioned in the ear flap 88 between an obstructing element 83 (elastic side panel member 90) and the topsheet 34. It can also be seen in FIG. 3 and FIG. 4, that the stretched elastic strands 105 have a coating of release agent 78 to protect this portion of the stretched elastic strands 105 from the elastic side panel member 90 and from the construction adhesive (not shown) which bonds the elastic side panel member 90 to the topsheet 34 and the backsheet 36. FIG. 4 additionally shows the elastic adhesive 51 which secures the stretched elastic strands 105 to the topsheet 34 and backsheet 36 in the crotch region 57. Upon severing, or otherwise relaxing, the stretched elastic strands 105 the end portions positioned in the ear flap 88 will become relaxed, inactive, and nonfunctional, while the portions secured to the crotch region 57 will contract or gather the crotch material to provide an elastic gasketing cuff 104.

In a preferred embodiment wherein the elastic strand is a continuous elastic strand intermittently joined to a continuous diaper web, the stretched, continuous elastic strands will be positioned between the continuous topsheet web and the continuous backsheet web such that the portions having only release agent applied thereto will be positioned in the waist regions of the webs and the portions having elastic adhesive applied thereto will be positioned in the crotch regions on the webs. The continuous backsheet web will have obstructing elements joined thereto, and is joined to the continuous topsheet web such that the obstructing elements are positioned in the waist regions and superpose the portions of the elastic strands having only release agent applied thereto. Thereafter, individual diapers will be severed from the continuous diaper web. A more detailed description of the manner in which the elastic strands may be positioned and secured to the diaper 80 can be found in U.S. Pat. No. 4,253,461 issued to Strickland and Visscher on Mar. 3, 1981 and the aforementioned U.S. Pat. No. 4,081,301 issued to Buell on Mar. 28, 1978, both of which are incorporated herein by reference.

The step of relaxing the elastic strand 105 is accomplished manually or by any other means well known in the art for releasing tension that has been created in an elastomeric element. In a preferred embodiment wherein the elastic strand 105 is a continuous elastic strand secured to a continuous diaper web, the elastic strand is relaxed when the individual diapers are severed from the diaper web. Upon severing the individual diapers from the web, the elastic strands are also severed and the tension is removed so that the elastic strands will relax or contract. The portion of the elastic strand positioned and secured in the crotch region 57 will contract or shirr the disposable diaper 80 in the crotch region 57 to form elastic gasketing cuffs 104. The portions of the elastic strands having release agent (indicated by the number 78 and FIGS. 3 and 4) applied thereto will become relaxed, inactive, and nonfunctional. The obstructing elements 83 will not adhere to, "grab", or otherwise restrain the adhesive-free end portions of the elastic strand 105 because of the presence of the release agent 78.

Thus, there has been provided, in accordance with the present invention, a method for adhering discrete portions of an elastomeric member to a substrate having obstructing elements joined thereto. It should be noted, however, that while particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for adhering discrete portions of an elastomeric member to a substrate having at least one obstructing element joined thereto, said method comprising the steps of:

providing a substrate having a first and second portion, at least part of said second portion of said substrate having at least one obstructing element comprising construction adhesive positioned thereon;

providing an elastomeric member in a stretched condition, said elastomeric member having a first portion and a second portion;

applying an elastic adhesive to said first portion of said elastomeric member;

applying a release agent to at least said second portion of said elastomeric member;

joining said elastomeric member to said substrate such that said first portion of said elastomeric member becomes joined to at least a portion of said first portion of said substrate and said second portion of said elastomeric member is disposed essentially on said second portion of said substrate, at least a part of said second portion of said elastomeric member superposing said obstructing element; and relaxing said elastomeric member such that said first portion of said elastomeric member contracts said first portion of said substrate and said second portion of said elastomeric member becomes relaxed, inactive and non-functional without becoming restrained by said obstructing element.

2. A method according to claim 1 wherein said adhesive applied to said first portion of said elastic member is unaffected by said release agent and wherein said step of applying a release agent comprises continuously coating said elastic member with said release agent such that since said adhesive is unaffected by said release agent, said elastic member is joined to said substrate by said adhesive.

3. A method according to claim 1 wherein said step of applying a release agent comprises intermittently coating said elastic member with said release agent.

4. A method according to claim 1 wherein said release agent is applied to said elastic member before said elastic adhesive is applied to said elastic member.

5. A method according to claim 1 wherein said elastic member is intermittently coated with said elastic adhesive after said release agent is applied to said elastic member.

6. A method according to claim 1 wherein said obstructing element consists of construction adhesive.

7. A method according to claim 1 wherein said obstructing element additionally comprises a layer of natural rubber foam.

8. A method according to claim 1 wherein said release agent is a mineral oil.

9. A method according to claim 1 wherein said substrate comprises a portion of a disposable diaper.

10. A method for manufacturing a disposable absorbent article having at least one obstructing element and having at least one elasticized leg cuff, said method comprising the steps of:

providing a chassis having end edges, longitudinal side edges; a periphery substantially adjacent said end edges and said longitudinal side edges; a first waist region; a second waist region; and a crotch region extending between said first waist region and said second waist region; said chassis comprising: a liquid pervious topsheet, a liquid impervious backsheet associated with said topsheet, and absorbent core positioned between said topsheet and said backsheet; and at least one obstructing element comprising construction adhesive joined to at least a portion of said second waist region of said chassis;

providing at least one elastomeric member in a stretched condition, said elastomeric member having a first portion and a second portion;

applying a release agent to at least said second portion of said elastomeric member;

applying an elastic adhesive to said first portion of said elastomeric member;

joining said elastomeric to a periphery of said chassis adjacent one of said longitudinal side edges such that at least part of said second portion superposes said obstructing element and said first portion becomes joined to at least a portion of said crotch region of said chassis; and relaxing said elastomeric member from a stretched condition so that said first portion of said elastomeric member contracts at least a portion of said crotch region and said second portion becomes relaxed, inactive, and non-functional without being restrained by said obstructing element.

11. The method of claim 10 wherein said adhesive applied to said first portion of said elastic member is unaffected by said release agent and wherein said step of applying said release agent to said elastomeric member comprises applying release agent to the entire length of said elastomeric member such that since said adhesive is unaffected by said release agent, said elastic member is joined to said substrate by said adhesive.

12. The method of claim 10 wherein said obstructing element comprises a layer of construction adhesive.

13. The method of claim 10 wherein said step of providing a chassis comprising at least one obstructing element joined to at least a portion of said second waist region, comprises providing a chassis comprising two obstructing elements, each of said obstructing elements being joined to said second waist region, substantially adjacent to opposite longitudinal side edges of said chassis.

14. A method for manufacturing a disposable absorbent article having obstructing elements and having a first and second elasticized leg cuff, said method comprising the steps of:

providing a chassis having end edges; a first longitudinal side edge; a second longitudinal side edge; a periphery substantially adjacent said end edges, said first longitudinal side edge, and said second longitudinal side edge; a first waist region having ear flaps; a second waist region having ear flaps; a crotch region extending between said first waist region and said second waist region; said chassis comprising a liquid pervious topsheet, a liquid impervious backsheet associated with said topsheet, an absorbent core positioned between said topsheet and said backsheet, at least one obstructing element comprising construction adhesive joined to at least the ear flaps of said second waist region; and at least one obstructing element comprising construction adhesive joined to at least the ear flaps of said first waist region;

providing a first elastomeric member and a second elastomeric member, said first elastomeric member and said second elastomeric member being in a stretched condition, said first elastomeric member and said second elastomeric member each having a first end portion, a second end portion, and a middle portion extending between said first end portion and said second end portion;

applying a release agent to at least first end portion and said second end portion of said first elastomeric member and said second elastomeric member;

applying an elastic adhesive to said middle portion of said first elastomeric member and said second elastomeric member;

joining said first elastomeric member and said second elastomeric member between said topsheet and said backsheet such that said first end portions superpose a portion of said obstructing element of said first waist region, said second end portions superpose a portion of said obstructing element of said second waist region, and said middle portions become joined to at least a portion of said crotch region, a middle portion of said first elastomeric member being joined in the periphery adjacent said first longitudinal side edge and the middle portion of said second elastomeric member being joined in the periphery adjacent said second longitudinal side edge;

relaxing said first elastomeric member and said second elastomeric member from a stretched condition so that: said first end portions become relaxed, inactive, and non-functional without being restrained by said obstructing element of said first waist region; said second end portions become relaxed, inactive, and non-functional without being restrained by said obstructing element of said second waist region; said middle portion of said first elastomeric member contracts a portion of the periphery adjacent said first longitudinal side edge to form a first elasticized leg cuff; and said middle portion of said elastomeric member contracts at least a portion of said periphery adjacent said longitudinal side edge to form a second elasticized leg cuff.

15. The method of claim 14 wherein said adhesive applied to said first portion of said elastomeric member is unaffected by said release agent and wherein said step of applying said release agent to at least said first elastomeric member and said second elastomeric member, comprises applying release agent to the entire length of said first elastomeric member and said second elastomeric member such that since said adhesive is unaffected by said release agent, said elastic member is joined to said substrate by said adhesive.

16. The method of claim 14 wherein said obstructing element of said first waist region and said obstructing element of said second waist region comprise a layer of construction adhesive.

17. A disposable absorbent article having elasticized leg bands and at least one obstructing element, said disposable absorbent article comprising:

a chassis having end edges; longitudinal side edges; a periphery substantially adjacent said end edges and said longitudinal side edges; a first waist region; a second waist region; and a crotch region extending between said first waist region and said second waist region; said chassis comprising: a liquid pervious topsheet, a liquid impervious backsheet joined with said topsheet, an absorbent core positioned between said topsheet and said backsheet;

at least one obstructing element comprising construction adhesive joined to at least a portion of said second waist region of said chassis;

two elasticized leg cuffs, each of said leg cuffs being joined to the periphery of said chassis adjacent one of said longitudinal side edges, each of said elasticized leg cuffs comprising at least one elastomeric member having a first portion which is operatively associated with at least a portion of said crotch region of said chassis, and a second portion which is relaxed, inactive, and non-functional, each said elasticized leg cuffs being formed according to the method comprising the steps of:

providing at least one elastomeric member in a stretched condition, said elastomeric member having a first portion and a second portion;

applying a release agent to at least said second portion of said elastomeric member; applying an elastic adhesive to said first portion of said elastomeric member;

joining said elastomeric member between said topsheet and said backsheet such that said at least a part of said second portion superposes said obstructing element and said first portion becomes joined to at least a portion of said crotch region of said chassis; and relaxing said elastomeric member from a stretched condition so that said first portion of said elastomeric member contracts at least a portion of said crotch region and said second portion becomes relaxed, inactive, and non-functional without being restrained by said obstructing element.

18. A disposable absorbent article having elasticized leg bands and at least two obstructing elements, said disposable absorbent article comprising:

a chassis having end edges; longitudinal side edges; a periphery substantially adjacent said end edges and said longitudinal side edges; a first waist region; a second waist region; and a crotch region extending between said first waist region and said second waist region; said chassis comprising:

a liquid pervious topsheet, a liquid impervious backsheet associated with said topsheet, an absorbent core positioned between said topsheet and said backsheet; and first and second obstructing elements comprising construction adhesive, said first obstructing element being joined to at least a portion of said first waist region, said obstructing element being joined to at least a portion of said second waist region;

two elasticized leg cuffs, each of said leg cuffs being joined to the periphery of said chassis adjacent one of said longitudinal side edges, each of said elasticized leg cuffs comprising at least one elastomeric member having a first portion which is operatively associated with at least a portion of said crotch region of said chassis, and a second portion which is relaxed, inactive, and non-functional, each said elasticized leg cuffs being formed to the method comprising the steps of:

providing at least one elastomeric member in a stretched condition, said elastomeric member having a first portion and an alternating second portion;

applying a release agent to at least said alternating second portion of said elastomeric member;

applying an elastic adhesive to said first portion of said elastomeric member;

joining said elastomeric member between said topsheet and said backsheet such that at least part of said alternating second portion superposes said first obstructing element, at least part of said alternating second portion superposes said second obstructing element, said first portion becomes joined to at least a portion of said crotch region of said chassis; and relaxing said elastomeric member from a stretched condition so that said first portion of said elastomeric member contracts at least a portion of said crotch region and said alternating second portion becomes relaxed, inactive, and non-functional without being restrained by said first and second obstructing element.

19. The disposable absorbent article of claim 17 wherein said obstructing element comprises a layer of construction adhesive.

20. The disposable absorbent article of claim 18 wherein said first and second obstructing elements comprise a layer of construction adhesive.

21. The disposable absorbent article of claim 18 wherein said first and second obstructing elements comprise a patch of natural foam.

* * * * *